United States Patent [19]

Lemke

[11] 4,445,644
[45] May 1, 1984

[54] DEVICE FOR DESTROYING HYPODERMIC NEEDLES AND SYRINGES

[76] Inventor: Walter G. Lemke, 3206 May Rd., El Sobrante, Calif. 94803

[21] Appl. No.: 273,410

[22] Filed: Jun. 15, 1981

[51] Int. Cl.³ .............................................. B02C 19/14
[52] U.S. Cl. .................................... 241/99; 241/190; 241/243
[58] Field of Search ................. 241/99, 100, 190, 243, 241/277, 279, 225, 294

[56] References Cited

U.S. PATENT DOCUMENTS 2,225,797 12/1940 Plauson ............................... 241/242
2,902,226 9/1959 Moore .................................. 241/100

Primary Examiner—Mark Rosenbaum
Assistant Examiner—Timothy V. Eley
Attorney, Agent, or Firm—Harris Zimmerman; Howard Cohen

[57] ABSTRACT

A device for destroying hypodermic needles and syringes includes a housing in which a pair of fixed blades are secured at their bases and supported in parallel, spaced apart relationship. A rotating shaft extends through aligned holes in the apices of the blades, and a trio of cylindrical members, each having a cylindrical blade secured thereto, is assembled on the shaft with each cylindrical blade adjacent to a fixed triangular blade. The cylindrical members and cylindrical blades are each provided with a slot extending radially therein, all of the slots being generally aligned in the axial direction. A syringe is introduced through an opening in the housing to rest in the aligned slots of the blades and cylindrical members. The shaft is rotated to cause the slot edges of the cylindrical blades to rotate past the fixed triangular blades, thereby shearing the syringe and needle.

5 Claims, 5 Drawing Figures

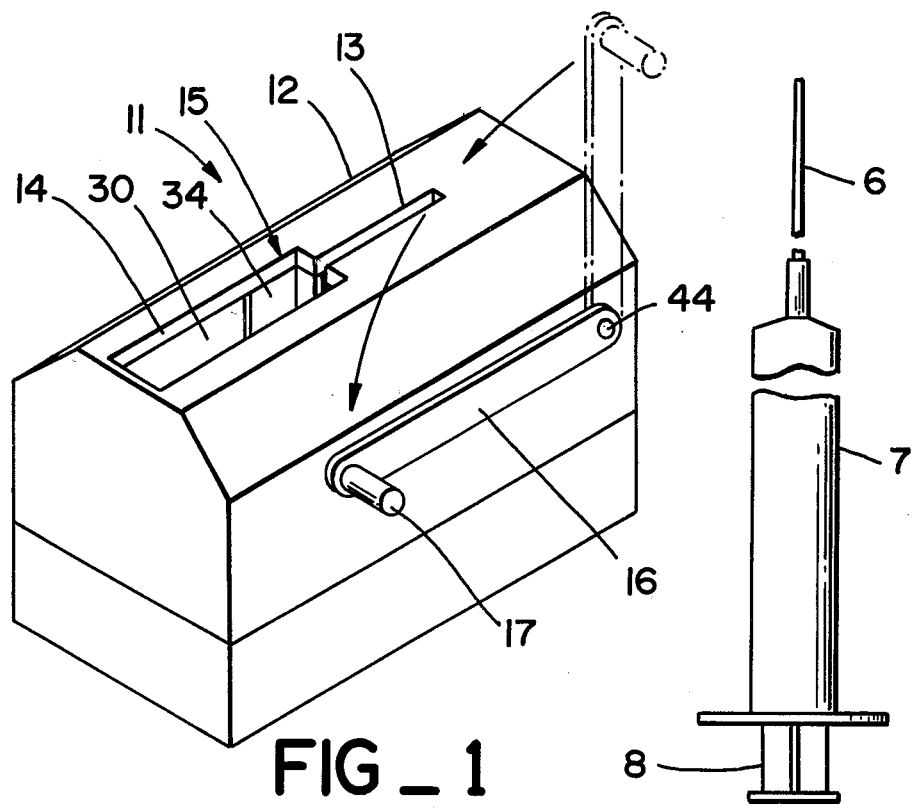
FIG_1
FIG_2
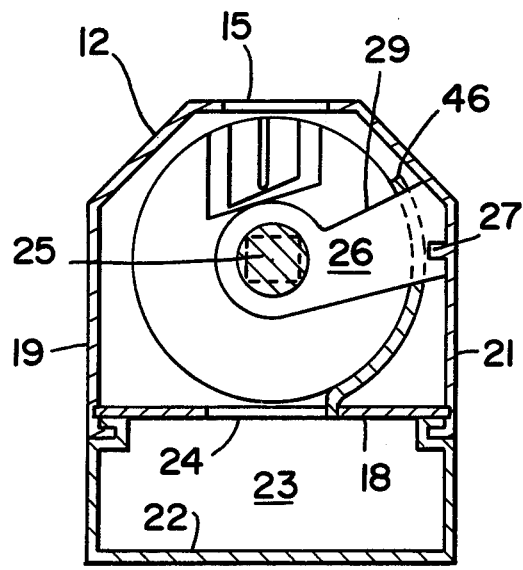
FIG_4
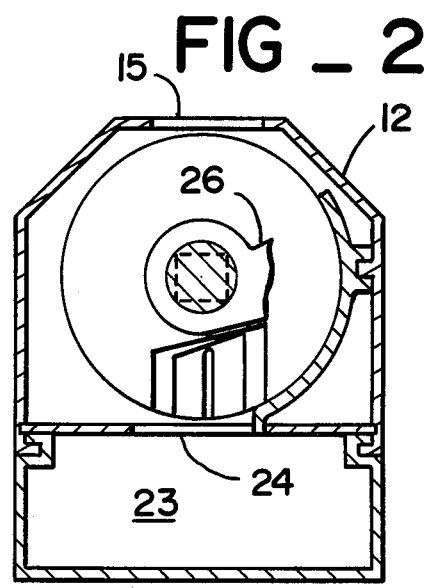
FIG_5

DEVICE FOR DESTROYING HYPODERMIC NEEDLES AND SYRINGES

BACKGROUND OF THE INVENTION

The following United States Patents comprise the most pertinent known prior art:

| | |
|---|---|
| 3,683,733 | 3,785,233 |
| 3,851,555 | 3,404,593 |
| 3,567,140 | 3,469,750 |
| 3,929,295 | 3,585,835 |
| 3,958,765 | |

According to some state laws recently enacted, disposable syringes are required to be substantially destroyed before being discarded. This step is required in order to prevent reuse of the syringes and needles and to eliminate the possible spread of diseases thereby.

The references cited in the foregoing disclose various devices for crushing or shearing syringes and needles to prevent their reuse. These devices may be characterized by their mechanical complexity, so that they require frequent maintenance and replacement of worn parts. Also, the prior art devices do not adequately protect the contaminated shards and debris which result from the destruction of the syringes and needles. This debris, which is extremely sharp and dangerous, often must be handled by the machine operator in order to effect disposal thereof. The operator of the machine thus is exposed to a substantial biological danger while disposing of the shards and debris.

SUMMARY OF THE PRESENT INVENTION

The present invention generally comprises a device for destroying hypodermic needles and syringes. Its most salient features include positive destruction of both the needle portion and the barrel portion of a hypodermic needle assembly, ease of operation, and controlled disposal of the resulting debris.

The device of the present invention includes a housing having an input slot therein, the input slot including a narrow portion at one end for receiving a hypodermic needle, and a wider portion aligned with the narrow portion and adapted to receive the cylinder and plunger of a syringe.

Supported within the housing is a pivot shaft which is generally aligned with the slot in the housing. A plurality of cylindrical members are assembled on the pivot shaft in coaxial fashion and are adapted to rotate therewith. A pair of disc-like cutting blades are secured coaxially to a pair of cylindrical members. The cylindrical members and the disc-like cutting blades are each provided with a slot extending radially inwardly from the periphery thereof and adapted to receive a portion of the syringe and hypodermic needle assembly.

The device also includes a pair of stationary blades having a generally triangular configuration and supported at the bases thereof. The stationary blades are each disposed directly adjacent to one of the disc-like blades, with the pivot shaft extending through aligned holes in the apices of the stationary blades. These stationary blades include an upper shearing surface which extends generally radially outwardly from the pivot shaft.

The radial slots of the cylindrical members and disc-like blades are disposed in longitudinal alignment, with the assembly being positioned so that the slots thereof are aligned with and open directly to the input slot of the housing. The housing includes a lateral inner wall disposed therein and spaced diametrically from the input slot of the housing. The inner wall defines a debris collecting chamber directly below the rotating assembly. A refuse slot extends through the inner wall in spaced-apart opposition to the input slot of the housing. A curved shield is disposed directly adjacent to the outer periphery of the assembled cylindrical members and disc-like blades, the shield extending from the debris slot almost to the input slot. The shield includes openings through which the fixed blades extend.

After a needle and syringe assembly is introduced into the input opening of the housing, it falls into the radial slots of the assembled cylindrical members and blades. The pivot shaft is then caused by manual or powered means to rotate toward the curved shield and the upper shearing edges of the stationary blades. As the radial slots of the rotating assembly pass the stationary blades, the edges of the radial slots intersect the upper shear edges of the stationary blades and shear the hypodermic assembly, thereby breaking the needle from the assembly and shearing the cylindrical portion of the assembly. The rotating assembly pivots approximately 180 degrees until it is aligned with the debris slot in the inner wall of the housing. The debris retained by the aligned radial slots and the curved shield falls into the debris collecting chamber.

BRIEF DESCRIPTION OF THE DRAWING

FIG. 1 is a perspective view of the device of the present invention for destroying hypodermic needle assemblies.

FIG. 2 is a plan view of a typical hypodermic needle assembly.

FIG. 4 is a cross-sectional elevation of the device of the present invention, shown in the intake position.

FIG. 5 is a cross-sectional elevation as in FIG. 4, shown partially rotated from the intake position.

DESCRIPTION OF THE PREFERRED EMBODIMENT

Figure 3:
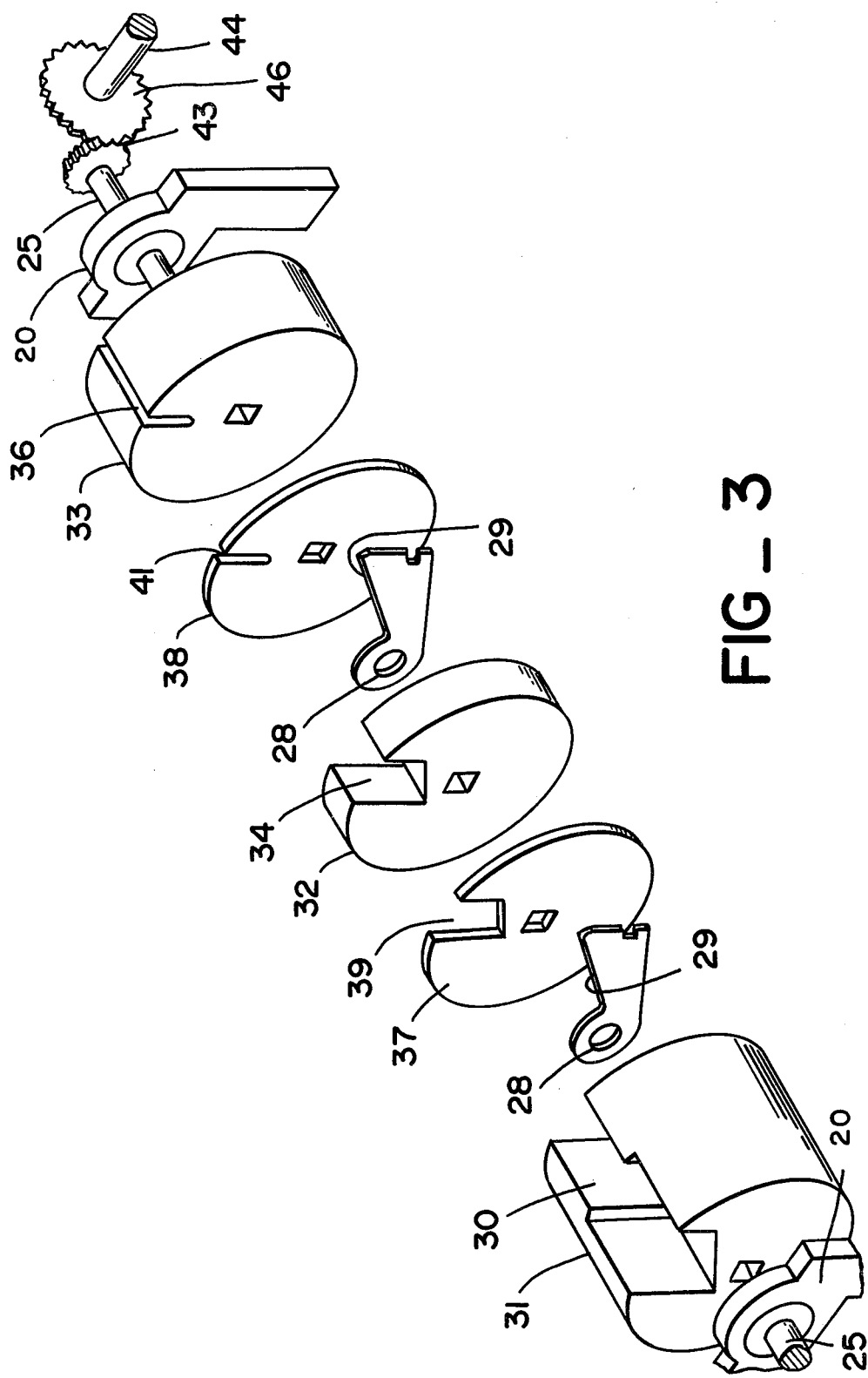
FIG. 3 is an exploded view of the shearing assembly of the present invention.

The present invention generally comprises a device for destroying and rendering completely unusable hypodermic needle and syringe assemblies. As shown in FIG. 2, a typical hypodermic assembly includes a hypodermic needle 6 which extends axially from a hollow cylindrical barrel 7, and a plunger 8 extends from the end of the barrel.

With reference to FIGS. 1, 4, and 5, the preferred embodiment of the present invention includes a generally rectangular housing 11 having a rectangular top surface 12. Disposed in the top surface 12 is an intake slot 15, the slot 15 including a long, narrow rectangular portion 13 opening onto and aligned with a long, wider rectangular portion 14. It may be appreciated that the slot 15 is configured to accomodate the outer dimensions of a typical syringe assembly, as shown in FIG. 2. Extending from one side of the housing 11 is a pivotable lever 16 having a handle at the distal end thereof for manual actuation.

Within the housing 11, an intermediate panel 18 extends between the opposed sidewalls 19 and 21, and is disposed parallel to the upper panel 12. The panel 18, the lower portions of the side walls 19 and 21, and a bottom wall 22 extending therebetween define a debris collection chamber 23 below the wall 18. An outlet slot 24 extends through the intermediate wall 18 to the chamber 23.

With reference to FIGS. 3, 4, and 5, the present invention includes a pivot shaft 25 which extends longitudinally within the housing 11 generally parallel to the slot 15. The shaft 25 is supported at both ends by a pair of bearing assemblies 26. A pair of stationary blades 26 are disposed within the housing 11, supported at like ends by a support bar 27 extending adjacent to the side wall 21. The blades 26 extend inwardly from the side wall 21, and are provided with axially aligned holes 28 through the inner ends thereof to receive the pivot shaft 25 therethrough. As shown in FIG. 3, the blades 26 are spaced apart along the axial extent of the shaft 25. The upper edge 29 of each blade 26 is hardened and ground to form a shearing edge.

The device also includes a trio of cylindrical members 31, 32, and 33. Each of the cylindrical members includes a square hole extending axially therethrough to receive a similar portion of the shaft 25. The members 31 and 32 are provided with generally trapezoidal slots 30 and 34 extending radially therein from the periphery and having a longitudinal extent parallel to the shaft 25. The cylindrical member 33 is provided with a generally U-shaped slot 36 which extends radially inwardly from the periphery and also has a longitudinal extent parallel to the shaft 25. The slot 36 in slightly narrower than the slots 33 and 34, as shown in FIG. 3.

A pair of cylindrical disc-like rotary blades 37 and 38 are secured to the cylindrical members 32 and 33, respectively. The rotary blade 37 includes a generally trapezoidal slot 39 extending radially therein and aligned with the slot 34 of the member 32. The slot 39 of the rotary blade in slightly narrower than the slot 34. Likewise, the blade 38 includes a slot 41 which is aligned with and slightly narrower than the slot 36 of the member 33. Both of the rotary blades 37 and 38 include square holes extending axially therethrough to receive the shaft 25.

The cylindrical member 31 is disposed beneath the wide portion 14 of the slot 15, as is the assembly consisting of the cylindrical member 32 and the blade 37. The assembly consisting of the cylindrical member 33 and the blade 38 is disposed directly beneath the narrow portion 13 of the slot 15.

Joined to one end of the shaft 25 is a bevel gear 43. A drive shaft 44 extends perpendicularly to the pivot shaft 25, and includes a bevel gear 46 supported on one end thereof which engages the bevel gear 43. In the preferred embodiment, the gear 46 is provided with twice the number of teeth of the gear 43. The distal end of the shaft 44 is joined to the proximal end of the lever 16.

The device also includes a curved shield 46 circumscribing an angular portion of the periphery of the pivot shaft assembly. The lower edge of the shield 46 is disposed directly adjacent to the slot 24 in the intermediate panel 18. The upper edge of the shield 46 is disposed substantially above the shear edges 29 of the blades 26. The shield 46, which is secured to bar 27 as shown in FIG. 5, is disposed to provide minimal rotational clearance for the rotating members assembled on the shaft 25.

When the lever 16 is raised by means of a handle 17 to the upright position shown in phantom line in FIG. 1, the slots 30, 34, 36, 39, and 41 are aligned so that they face upwardly and open to the intake opening 15 of the housing 11. In this disposition, a syringe as shown in FIG. 2 may be dropped into the intake opening 15 and be cradled in the upwardly opening slots of the respective rotating members. The handle 17 is then pulled forwardly and downwardly as shown by the arrow in phantom, so that the rotating assembly begins to rotate clockwise as shown in FIG. 5. As the upwardly aligned slots of the rotating members rotate away from the intake opening 15, it may be appreciated that the opening 15 becomes blocked by the circumferential surfaces of the rotating members and blades. This is a safety feature which prevents any manual interference with the shearing operation to follow.

When the slots 39 and 41 of the blades 37 and 38, respectively, intersect the shearing edges 29 of the stationary blades 26, they cause a shearing action which cuts through the barrel portion 7 and the needle portion 6 of the syringe assembly. The plunger member 8 is also sheared, so that the respective parts of the syringe assembly are completely destroyed and rendered entirely unusable.

The debris which results from the shearing action of the rotating blades 37 and 38 and the stationary blades 26 is retained within the slots 33, 34, and 36 of the respective rotating members, due to the position and extent of the curved shield 46. When the rotating assembly has rotated approximately 90 degrees, the aligned slots move into open communication with the discharge opening 24 of the intermediate panel 18. The debris then falls gravitally into the refuse collection chamber 23 within the housing 11.

It may be appreciated that the 180 degree rotation of the rotating assembly is caused by an approximately 90 degree rotation of the lever 16, due to the ratio of the number of teeth of the gear 46 and the gear 43. The slot 15 remains generally occluded by the peripheral surfaces of the rotating assembly, so that no foreign object can be introduced into the device, and no manual interference may be obtained with the debris of the shearing operation. When the device is to be used once more, the lever 16 is once again raised to the upright position to align the slots of the rotating assembly with the intake slot 15.

It may be appreciated that the mechanism of the present invention is simple yet absolutely effective in destroying a syringe assembly. Furthermore, the debris resulting from the destruction of the syring assembly is entirely contained within the chamber 23. Thus the disposal of the debris may be achieved without directly handling the debris. This may be accomplished by means of a port in the housing communicating with the chamber 23. Alternatively, a removable bin or receptacle may be disposed within the chamber 23 to collect the debris and facilitate disposal thereof.

I claim:

1. A device for destroying hypodermic needle and syringe assemblies, comprising a housing, an intake opening in said housing adapted to receive a syringe assembly therein; a pivot shaft in said housing adjacent to said intake opening; a plurality of disc-like rotating blades secured to said pivot shaft and spaced therealong, each of said rotating blades including a slot extending radially inwardly from the periphery thereof, a plurality of fixed blades, each disposed directly adjacent to one of said rotating blades and including a shearing edge past which said slot is rotatable, means for rotating said shaft and blade assembly from a first position in which said slots open toward said intake opening, past a second position in which said slots intersect said shearing edges of said fixed blades, to a third position in which the sheared hypodermic assembly debris is discharged from said slots, and a plurality of cylindrical members assembled axially on said shaft, each secured adjacent to one of said disc-like blades and having substantially the same diameter, each of said cylindrical members including a slot extending into the periphery thereof and aligned with the slot of the respective blade, said slot adapted to receive and retain a portion of the syringe assembly.

2. The device of claim 1, further including a debris colleting chamber within said housing, and a discharge opening extending from said debris collecting chamber to said third position of said shaft and blade assembly.

3. The device of claim 1, wherein said means for rotating said pivot shaft includes a handle extending from said housing and secured to a handle shaft.

4. The device of claim 1, wherein said intake opening includes a narrow slot portion for receiving the hypodermic needle and a wider slot portion for receiving the syringe, said slot portions being aligned longitudinally.

5. The device of claim 1, wherein said fixed blades are supported at their proximal ends, and further including a pivot shaft hole extending through the distal end of each of said fixed blades to support said pivot shaft extending therethrough in freely rotating fashion.

* * * * *